United States Patent [19]
Faiman et al.

[11] Patent Number: 6,156,794
[45] Date of Patent: Dec. 5, 2000

[54] METHOD FOR TREATMENT OF GLUTAMATE RELATED DISORDERS

[76] Inventors: Morris Faiman, 6318 W. 128th Pl., Overland Park, Kans. 66209; John V. Schloss, 4411 Gretchen Ct., Lawrence, Kans. 66047; Jang-Yen Wu, 1113 Wellington Rd., Lawrence, Kans. 66049

[21] Appl. No.: 09/297,803
[22] PCT Filed: Nov. 6, 1997
[86] PCT No.: PCT/US97/20308
  § 371 Date: Sep. 13, 1999
  § 102(e) Date: Sep. 13, 1999
[87] PCT Pub. No.: WO98/19676
  PCT Pub. Date: May 14, 1998

Related U.S. Application Data

[60] Provisional application No. 60/030,046, Nov. 6, 1996.
[51] Int. Cl.[7] ............. A61K 31/325; C07D 277/34; C07D 277/36; C07D 279/06
[52] U.S. Cl. .................. 514/478; 514/665; 544/54; 548/182; 560/302
[58] Field of Search ............... 514/478, 665; 548/182; 544/54; 560/302

[56] References Cited

U.S. PATENT DOCUMENTS

| | | | |
|---|---|---|---|
| 3,006,919 | 10/1961 | Gaul et al. | 548/182 |
| 3,215,704 | 11/1965 | Kinstler et al. | 548/182 |
| 3,679,516 | 7/1972 | Reece et al. | 544/47 |
| 4,148,800 | 4/1979 | Schubart et al. | 548/182 |
| 4,786,746 | 11/1988 | Miljkovic | 560/302 |
| 5,153,219 | 10/1992 | Faiman et al. | 514/478 |

OTHER PUBLICATIONS

Hanefeld et al., Arkiv Der Pharmazie, 318(1), 1985, 60–69.

Piper et al., J. Org. Chem., 28(4), 1963, 981–985.

Database Medline on STN, U.S. National Library of Medicine (Bethesda, MD, USA), No. 96306257, Hugon, H. J. et al., "Role of Glutamate and Excitotoxicity in Neurologic Diseases", abstract, 1996.

*Primary Examiner*—Fiona T. Powers
*Attorney, Agent, or Firm*—Schwegman, Lundberg, Woessner & Kluth, P.A.

[57] ABSTRACT

A method of using a compound of formula (I) wherein $R^1$, $R^2$, $R^3$, X and n have any of the meanings defined in the specification, to antagonize glutamate binding, or to treat glutamate-related disorders is provided. Novel compounds, intermediates and pharmaceutical compositions are also provided.

35 Claims, 8 Drawing Sheets

Key:
DSF: Disulfiram
DETC-MeSO: S-methyl N,N-diethylthiolcarbamte Sulfoxide
NBI: N-butyl imidazole

KEY:

DMTC-SO: S-methyl N,N-dimethylthiolcarbamate Sulfoxide

DETC-SO: S-methyl N,N-diethylthiolcarbamate Sulfoxide  (DETC-MeSO)

DPTC-SO: S-methyl N,N-dipropylthiolcarbamate Sulfoxide

DBTC-SO: S-methyl N,N-dibutylthiolcarbamate Sulfoxide

ALDH   : Aldehyde Dehydrogenase

Key:
DETC-MeSO: S-methyl N,N-diethylthiolcarbamate Sulfoxide
DETC-GS  : N,N-diethyl-S-carbamoyl-glutathione

DMTC-SO

DETC-SO

DPTC-SO

DBTC-SO

METHOD FOR TREATMENT OF GLUTAMATE RELATED DISORDERS

This application is a 371 of PCT/US97/20308 filed Nov. 6, 1997 and claims the benefit of provisional application U.S. Ser. No. 60/030,046 filed Nov. 6, 1996.

This invention was made with U.S. Government support under grant N00014-94-1-0457 from the Office of Navel Research. The U.S. Government has certain rights in this invention.

BACKGROUND OF THE INVENTION

Thiamine deficiency has long been known to cause neurological disorders, such as Wernicke-Koraskoff syndrome or cerebral beriberi. Many of the symptoms of Wernicke-Korsakoff syndrome parallel those of Alzheimer's disease, in particular with respect to loss of memory, mental confusion and dementia. The gene for early-onset familial Alzheimer's disease has recently been identified to be coincident with the position (14q24.3) of the gene encoding the human E2k component (dihydrolipoyl succinyl transferase) of the α-ketoglutarate dehydrogenase (KDH) complex, a thiamine pyrophosphate-dependent enzyme system (Ali et al., 1994; Nakano et al., 1994). This chromosomal position is also associated with another inherited neurological disorder, Machado-Joseph disease. The neurological damage associated with thiamine deficiency is thought to be due to an increase in extracellular glutamate levels during periods of KDH depression (Hazell et al., 1993; Heroux & Butterworth, 1995). Furthermore, glutamate toxicity is believed to be involved in many neurodegenerative diseases, e.g., Alzheimer's disease, parkinsonism, stroke, and epilepsy, as well as hypertension, hypoglycemia and mental disorders such as schizophrenia.

Considerable effort has been devoted to discovery of glutamate antagonists (B. Scatton, *Life Sciences*, 55, 2115–2124 (1994); S. A. Lipton et al., *N. Engl. J. Med.*, 330, 613–622 (1994)) in recent years, due to increasing evidence linking glutamate excitotoxicity to various neurological disorders (R. J. Thomas, *J. Am. Geriatr. Soc.*, 43 1279–1289 (1995)). Unfortunately, while known antagonists can provide neuroprotection, excessive action of these classical blocking agents can obtain undesirable side effects (Scatton, supra; Lipton et al. (1994), supra). To minimize these undesirable side effects, modification of the redox modulatory sulfhydryl groups of the glutamate receptor has been suggested as a possibly superior therapeutic strategy (H. Gozlan et al., *TiPS*, 16, 368–374 (1995)). Unlike classical antagonists that can give complete inhibition by interaction at the glutamate receptor (e.g., CGS 19755) or directly at receptor-linked, calcium ion channels (e.g., phencyclidine or MK-801) (Lipton et al. (1994), supra) inhibition via the redox modulatory sites are expected to give only partial inhibition of function and thereby limit unwanted side effects associated with excessive antagonism (Gozlan, supra). At present S-nitrosylation of glutamate receptors by an $NO^+$ donor (e.g., nitroglycerin) is the only mechanism for partially blocking receptor response in vivo, that would achieve this effect by interaction with the redox modulatory sites (S. A. Lipton et al., *Nature* (London), 364, 626–632 (1993); S. A. Lipton, *Neurochem.*, 29, 111–114 (1996)).

Thus, a need exists for a method to treat glutamate-related disorders (such as glutamate-related neurodegenerative disorders) with non-toxic glutamate antagonists.

SUMMARY OF THE INVENTION

The present invention provides a therapeutic method comprising preventing or treating a glutamate-related disorder in a mammal, by administering to said mammal an effective amount of a compound of the formula I:

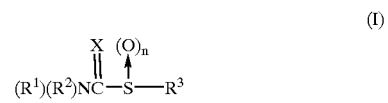

wherein
a) $R^1$ and $R^2$ are individually $(C_1-C_8)$ alkyl, $(C_6-C_{12})$aryl, or heteroaryl; or $R^1$ and $R^2$ together with the nitrogen to which they are attached are a 4–8 membered ring optionally comprising 1, 2, or 3 additional heteroatoms selected from the group consisting of non-peroxide oxygen, sulfur, and $N(R_a)$,
wherein each $R_a$ is absent or is hydrogen, $(C_1-C_8)$alkyl, $(C_1-C_8)$alkanoyl, phenyl, benzyl, or phenethyl; and $R^3$ is hydrogen, $(C_1-C_8)$alkyl, $(C_6-C_{12})$aryl, heteroaryl, $SC(=S)N(R^1)(R^2)$, or a glutathione derivative; or
b) $R^1$ and $R^3$ together are a divalent ethylene or propylene chain and $R^2$ is $(C_1-C_8$ alkyl, $(C_6-C_{12})$aryl, or heteroaryl; or
c) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene ($-CH_2-$), ethylene ($-CH_2CH_2-$), or a direct bond; and wherein the ring comprising $R_b$ and $R^3$ is a five- or six-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;
X is O or S; and
n is 0, 1, or 2;
or a pharmaceutically acceptable salt thereof.

The invention also provides a method comprising inhibiting or preventing glutamate binding in a mammalian (for example human) tissue by contacting said mammalian tissue, in vitro or in vivo, with an amount of a compound of formula (I), or a pharmaceutically acceptable salt thereof, wherein the amount is effective to block or reduce the binding of glutamate to its receptor in said tissue.

The invention also provides the use of a compound of formula (I), or a pharmaceutically acceptable salt thereof, to prepare a medicament useful to treat a glutamate-related disorder.

The invention also comprises novel compounds and novel pharmaceutical compositions disclosed herein, as well as intermediates and processes useful for preparing compounds of formula (I). The invention also provides compounds of formula (I) for use in medical therapy.

DETAILED DESCRIPTION OF THE INVENTION

Figure 1:
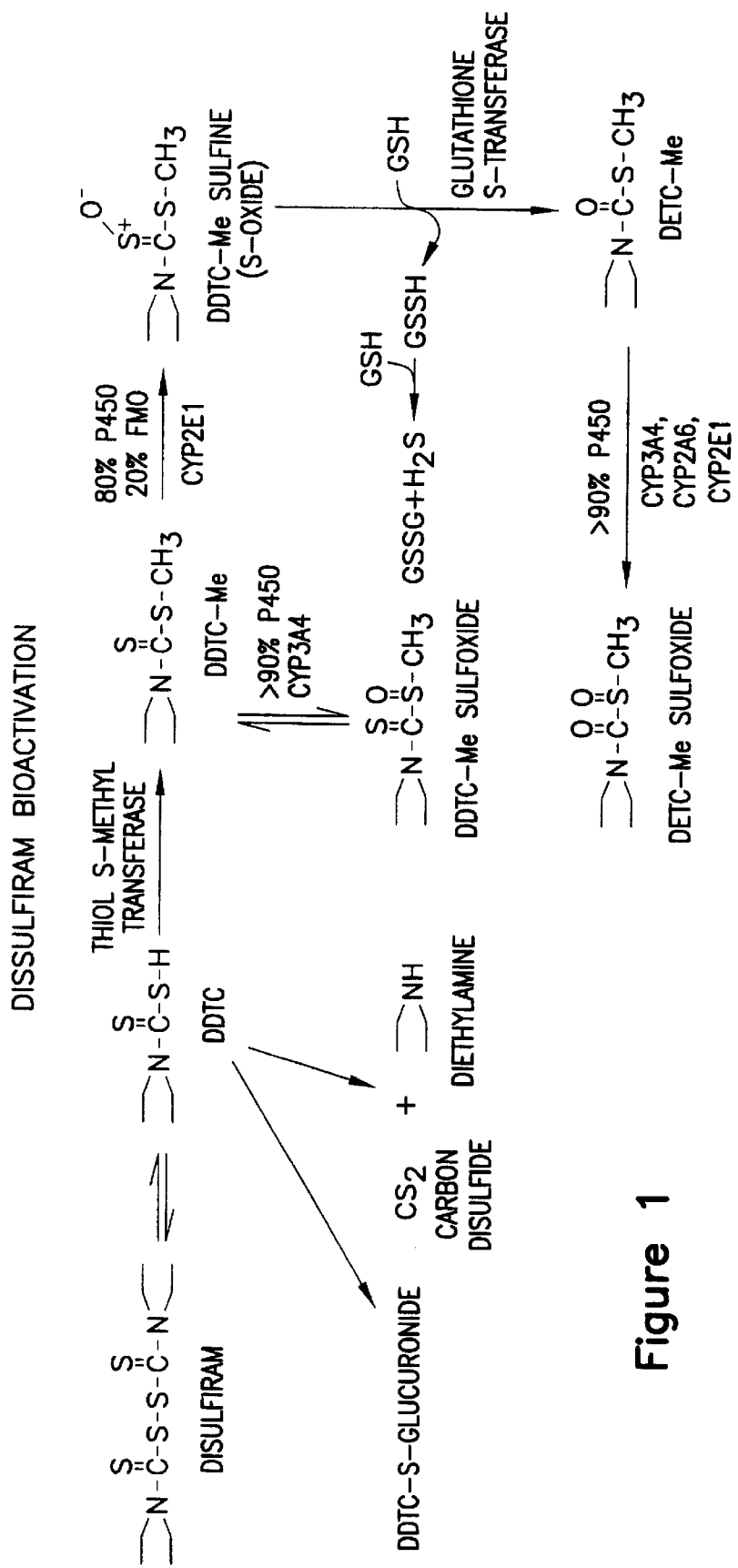
FIG. 1 depicts the bioactivation of disulfiram.

The following definitions are used herein. Halo is fluoro, chloro, bromo, or iodo. Alkyl includes both straight- or branched-chain alkyl, as well as cycloalkyl and (cycloalkyl)alkyl. Aryl denotes a phenyl radical or an ortho-fused bicyclic carbocyclic radical in which at least one ring is aromatic. Aryl includes aralkyl, alkaryl and alkaralkyl. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(Y) wherein each Y is absent or is H, O, ($C_1$–$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. As used herein, the term "glutathione derivative" means a compound of the formula:

Specific and preferred values listed below for radicals, substituents, and ranges, are for illustration only and they do not exclude other defined values or other values within defined ranges for the radicals and substituents.

Specifically, ($C_1$–$C_8$)alkyl can be methyl, ethyl, propyl, isopropyl, butyl, iso-butyl, sec-butyl, pentyl, 3-pentyl, hexyl, heptyl, octyl, cyclopropylmethyl, cyclopropyl, cyclopentyl, or cyclohexyl; ($C_1$–$C_8$)alkoxy can be methoxy, ethoxy, propoxy, isopropoxy, butoxy, iso-butoxy, sec-butoxy, pentoxy, 3-pentoxy, hexyloxy, heptyloxy, or octyloxy; ($C_1$–$C_8$)alkanoyl can be acetyl, propanoyl, butanoyl, isobutanoyl, pentanoyl, hexanoyl, heptanoyl, or octanoyl; and ($C_2$–$C_8$)alkanoyloxy can be acetoxy, propanoyloxy, butanoyloxy, isobutanoyloxy, pentanoyloxy, hexanoyloxy, heptanoyloxy, or octanoyloxy. Aryl can be phenyl, indenyl, benzyl, or naphthyl. Heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Preferably, alkyl is ($C_1$–$C_4$)alkyl and aryl is phenyl or benzyl.

A specific group of compounds are compounds of formula I wherein $R^1$ and $R^2$ together with the nitrogen to which they are attached are a ring selected from the group consisting of azetidino, pyrrolidino, piperidino, hexamethyleneimin-1-yl, and heptamethyleneimin-1-yl. Another specific group of compounds are compounds of formula I wherein $R^1$ and $R^3$ together are a divalent ethylene or propylene chain and $R^2$ is ($C_1$–$C_8$) alkyl, ($C_6$–$C_{12}$)aryl, or heteroaryl. A third specific group of compounds are compounds of formula I wherein $R^1$ and $R^2$ together with the nitrogen to which they are attached are an azetidino, pyrrolidino, piperidino, hexamethyleneimin-1-yl, or heptamethyleneimin-1-yl ring, said ring being substituted on carbon by a substituent $R_b$; wherein $R_b$ and $R^3$ taken together are a divalent ethylene or propylene chain.

A prefered group of compounds are compounds of formula I wherein $R^1$ and $R^2$ are individually ($C_1$–$C_8$) alkyl, or ($C_6$–$C_{12}$)aryl; $R^3$ is ($C_1$–$C_8$)alkyl, hydrogen, SC(=S)N($R^1$)($R^2$) or a glutathione derivative; X is O or S; n is 0 or 1 or a pharmaceutically acceptable salt thereof.

Another preferred group of compounds are compounds of formula I wherein $R^3$ is ($C_6$–$C_{12}$)aryl or heteroaryl and n is 0.

As used herein, the term "glutamate-related disorder" comprises: a) neurodegenerative diseases associated with elevated levels of extracellular glutamate, including Huntington's disease, Alzheimer's disease, Parkinson's disease, aquired immunodeficiency syndrome (AIDS), epilepsy, nicotine addiction, cerebral ischemia (stroke), and familial Amyotrophic Lateral Sclerosis (ALS); as well as neurodegenerative diseases associated with thiamine deficiency, such as Wernicke-Korsakoff syndrome, cerebral beriberi, Machado-Joseph disease, Soshin disease, and related diseases such as those disclosed by Thomas et al., *J. Am. Geriatr. Soc.*, 43, 1279 (1995); and b) other diseases or conditions wherein glutamate activity is implicated, such as anxiety, glutamate related convulsions, hepatic encephalopathy, neuropathic pain, domoic acid poisoning, hypoxia, anoxia, mechanical trauma to the nervous system, hypertension, alcohol withdrawal seizures, alcohol addiction, alcohol craving, cardiovascular ischemia, oxygen convulsions, and hypoglycemia.

Some compounds of formula (I) have been shown to be potent inhibitors of rat liver mitochondrial low Km aldehyde dehydrogenase (see U.S. Pat. No. 5,153,219, the examples of which are described hereinbelow in Examples 1–6). For example, preferred compounds for use in the practice of the invention include those wherein X is O, $R^1$ and $R^2$ are individually ethyl or methyl and $R^3$ is methyl. More preferably, $R^1$=$R^2$=methyl or ethyl, e.g., the compound is S-methyl-N, N-diethylthiolcarbamate sulfoxide (DETC-Me sulfoxide) or S-methyl-N, N-diethyldithiocarbamate sulfoxide (DDTC-Me sulfoxide). Preferred compounds for use in the practice of the invention are substantially more bioactive than disulfiram, less toxic than the parent compounds and do not require bioactivation by the P450 liver enzyme system as do the metabolic precursors.

Pharmaceutically acceptable salts of the compounds of formula (I) include the nontoxic addition salts with organic and inorganic acids, such as the citrates, bicarbonates, malonates, tartrates, gluconates, hydrochlorides, sulfates, phosphates, and the like. All percentages are weight percentages unless otherwise indicated.

The compounds of formula I, wherein n=1 or 2, may be readily prepared by oxidation of the corresponding thiol esters of formula II:

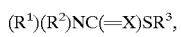

wherein X, $R^1$, $R^2$, and $R^3$ are as described hereinabove.

Thiol esters of formula (II) wherein X=O and $R^1$ and $R^2$ are individually ($C_1$–$C_8$)alkyl, ($C_6$–$C_{12}$)aryl, or heteroaryl; or wherein $R^1$ and $R^2$ together with the nitrogen to which they are attached are a 4–8 membered ring as described hereinabove, may be prepared by the bubbling carbonylsulfide into a mixture of triethylamine and the requsite amine of formula $(R^1)(R^2)NH$, in a suitable solvent, such as t-butanol. In situ alkylation with the requsite iodide of formula $R^3I$, yields the corresponding thiol ester of formula II.

Dithiocarbamates of formula II (X=S) can be prepared using techniques that are well known in the art, for example, as disclosed by M. Faiman et al., *Alcoholism*, 7, 307 (1983). The final products can be purified by chromatography on silica gel. Useful methods for preparing compounds of the invention are also disclosed in U.S. Pat. No. 5,035,878, issued Jul. 30, 1991.

Compounds of formula (I), wherein $R^1$ and $R^3$ together are a divalent ethylene or propylene chain and $R^2$ is $(C_1-C_8)$ alkyl, $(C_6-C_{12})$aryl, or heteroaryl; or compounds of formula (I) wherein $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene (—CH$_2$—), ethylene (—CH$_2$CH$_2$—), or a direct bond; and wherein the ring comprising $R_b$ and $R^3$ is a five- or a six-membered ring; can be prepared by condensing carbonyl chloride with the requsite precursor comprising an amine and a mercaptan. Conversion of the carbamoyl thioester to a sulfoxide can be carried out using techniques that are well known in the art, for example, as disclosed by M. Faiman et al., *Alcoholism*, 7, 307 (1983).

In clinical practice, one or more of the compounds of formula I, or the salts thereof, will normally be administered orally in the form of a pharmaceutical unit dosage form comprising the active ingredient in combination with a pharmaceutically acceptable carrier which may be a solid, gelled or liquid diluent or an ingestible capsule. A unit dosage to the compound or its salt may also be administered without a carrier material. As examples of pharmaceutical preparations may be mentioned tablets, hard or soft gelatin capsules, aqueous solutions, suspensions, and liposomes and other slow-release formulations, such as shaped polymeric gels.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dosage form in ampules, prefilled syringes, small volume infusion containers or multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506; and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122; 4,383,529; or 4,051,842.

Formulations suitable for topical administration in the mouth include unit dosage forms such as lozenges comprising active ingredient in a flavored base, usually sucrose and acadia or tragacanth; pastilles comprising the active ingredient in an inert base such as gelating and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened of melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoromethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the compounds can be administered as drops, gels (see, S. Chrai et al., U.S. Pat. No. 4,255,415), gums (see S. L. Lin et al., U.S. Pat. No. 4,136,177) or via a prolonged-release ocular insert (see A. S. Michaels, U.S. Pat. No. 3,867,519) and H. M. Haddad et al., U.S. Pat. No. 3,870,791).

Pharmaceutical compositions of the invention may also contain other adjuvants such as flavorings, colorings, antimicrobial agents, or preservatives.

It will be further appreciated that the amount of the present compound(s), or an active salt or derivative thereof, required for use in treatment will vary not only with the particular salt selected but also with the route of administration, the nature of the condition being treated and the age and condition of the patient and will be ultimately at the discretion of the attendant physician or clinician.

Usually the active substance will comprise between about 0.005 and 99%, or between 0.1 and 95% by weight of the unit dosage form, for example, between about 0.1 and 50% of preparations intended for oral administration.

The amount of the compound of formula I that is administered and the frequency of administration to a given human patient will depend upon a variety of variables related to the patient's psychological profile and physical condition. For evaluations of these factors, see J. F. Brien et al., *Europ. J. Clin. Pharmacol.*, 14, 133 (1978); and *Physicians' Desk Reference*, Charles E. Baker, Jr., Pub., Medical Economics Co., Oradell, N.J. (41st ed., 1987). Generally, the dosages of the present compounds will be smaller than that administered in the case of disulfiram which is presently administered at 4–8 mg/kg orally, or than putative dosages of DETC-Me.

Disulfiram has been used in the treatment of alcoholism for almost 50 years (J. Hald et al., *Lancet*, 2, 1001–1004 (1948); M. D. Faiman, *Biochemistry and Pharmacology of Ethanol*, Volt 2., eds. Majchrowicz, E. and Novel, E. P., pp. 325–348, Plenum Press, New York). It has recently been demonstrated that disulfiram exerts its anti-alcohol effect in vivo only after bioactivation to the active metabolite S-methyl-N,N-diethylthiocarbamate sulfoxide (DETC-MeSO) (A. Madan et al., *Drug Metab. Dispos.*, 23, 1153–1162 (1995)), that is a potent and selective carbamoylating agent for sulfhydryl groups (L. Jin et al., *Chem. Res. Toxicol.* 7, 526–533 (1994). However, disulfiram is known to produce a number of unwanted neurological side-effects.

Not all of the adverse neurological effects of disulfiram can be attributed to modification of glutamate receptors. Disulfiram is metabolized to carbon disulfide, a known neurotoxin, and potently inhibits copper enzymes, such as superoxide dismutase and dopamine β-hydroxylase, through the action of another disulfiram metabolite, diethyldithiocarbamate (T. J. Haley, *Drug Metab. Rev.*, 9, 319–335 (1979); D. I. Eneanya et al., *Ann. Rev. Pharmacol. Toxicol.*, 21, 575–596 (1981)).

DETC-MeSO does not share any of these latter effects with disulfiram, such as carbon disulfide formation or copper-enzyme inhibition, so it would be expected to more selectively affect glutamate receptors in vivo. In particular, DETC-MeSO is not likely to cause the seizures, optic neuritis and peripheral neuropathy linked to higher doses (>500 mg/day) of disulfiram, that are most probably a consequence of $CS_2$ formation (C. M. Fisher, *Arch. Neurol.*, 46, 798–804 (1989); B. Mokri et al., *Neurology*, 31, 73–735 (1981); H. R. Hotson et al., *Arch. Neurol.*, 33, 141–142 (1976)).

The invention will be further described by reference to the following detailed examples.

EXAMPLE 1
S-Methyl-N, N-Diethylthiolcarbamate (DETC-Me)

DETC-Me was synthesized employing a modification of the method of P. Klason, *J. Prak. Chemie*, 36, 67 (1887). Carbonyl sulfide, produced by dripping saturated KSCN into 48% sulfuric acid, was bubbled into a mixture of 11.3 ml of triethylamine and 7.7 ml of diethylamine in 100 ml of t-butyl alcohol in a 250 ml round bottom flask. The solution was stirred as the gas bubbled through the amine solution, with the reaction proceeding for 15 to 20 hours. The reaction was terminated by adding 5 ml of methyl iodide to form the final methylated product. The reaction mixture turned yellow and 15 to 20 minutes later a white precipitate formed. After 45 minutes, the reaction mixture was filtered and the alcohol and other volatile materials were evaporated. The remaining oil phase was dissolved in methylene chloride and extracted with 10% HCl, saturated $NaHCO_3$ and brine. The resulting organic phase was dried over sodium sulfate, and evaporated in vacuo. The resulting product was purified by medium pressure liquid chromatography (C-18 Sepralite® 40 μM, mobile phase 60:40 acetonitrile (Fisher Scientific, HPLC grade): water). Fractions containing the DETC-Me were extracted with methylene chloride. The organic phase was dried with sodium sulfate and solvent removed under reduced pressure. The product (about 4 g) was a pale yellow oil. The structure verified by TLC, NMR [$^1$H NMR (80 MHz, $CDCl_3$), δ3.35 (q,J=7 Hz,2H), δ2.50 (s,3H), δ1.15 (t,J=8 Hz,3H)], and mass spectroscopy [EIMS M/Z (relative intensity) 147 ($M^+$,13), 100 (75), 75 (24), 72 (100), 44 (69)].

EXAMPLE 2
S-Methyl-N, N-Diethylthiolcarbamate Sulfoxide (DETC-Me Sulfoxide)

DETC-Me (600 mg) was added to a suspension of 0.865 g of sodium metaperiodate (Aldrich Chem. Co.) in 8 ml of 1:1 methanol-water at 25° C. After 48 hours of stirring at 25° C., the reaction mixture was extracted with $CH_2Cl_2$. The organic layer was dried with sodium sulfate and the solvent removed under reduced pressure. The crude product was dissolved in a minimum amount of 1:1 acetonitrile-$H_2O$ and purified by medium pressure chromatography (C-18 Sepralite® 40 μM mobile phase 1:1 acetonitrile-$H_2O$. Fractions containing DETC-Me sulfoxide were pooled and extracted with methylene chloride. The solvent was dried with sodium sulfate and removed under reduced pressure to yield 0.46 g of DETC-Me sulfoxide as a yellowish oil; [$^1$H NMR (500 MHz, $CDCl_3$) 3.5696–3.4661 (m, 2H), 3.4428–3.3850 (m, 2H), 2.7082 (s,3H), 1.2257 (t, 3H, J=7.12 Hz), 1.1698 (t, 3H, J=7.09 Hz); mass spectroscopy: CIMS ($NH_3$) M/Z (relative intensity), 164 ($M^{+1}$, 13), 148 (3), 100 (100), 72 (86), 44 (82); IR (neat): 2980, 1690, 1420, 1255, 1210, 1065, 1035 $cm^{-1}$].

EXAMPLE 3
S-Methyl-N, N-Diethyldithiocarbamate Sulfoxide

S-Methyl-N, N-diethyldithiocarbamate sulfoxide (DDTC-Me SO) was prepared from S-Methyl-N, N-diethyldithiocarbamate (DDTC-Me). The synthesis of DDTC-ME was carried out as described by M. D. Faiman et al., *Alcoholism*, 7, 307 (1983), Sodium metaperiodate (200 mg) (Sigma Chemical Co.) was dissolved in 25 ml of 50:50 MeOH:$H_2O$ at 0° C. DDTC-Me (200 mg) was separately dissolved in 2 ml of methanol, and was then cooled to 0° C. before addition to a constantly stirring solution of sodium metaperiodate in MeOH:$H_2O$. The reaction mixture was stirred for 24 hr at 0° C. and then was diluted to 100 ml with cold 0.1 M potassium phosphate buffer (ph 7.4). The resulting colorless solution was then extracted with methylene chloride. The organic layer was treated with activated charcoal, and the charcoal was removed by filtration through a Celite bed. The solvent was removed under reduced pressure to obtain the crude product which was then purified by preparative HPLC (C-18, 5 micron, 150 mm×10 mm column, Alltech) using 30:70 acetonitrile:$H_2O$ (acetonitrile, Fisher Scientific, HPLC grade) at a flow rate of 2.5 ml/min. The fractions containing the DDTC-Me SO were pooled and diluted with four times the original volume with water. The diluted pooled fractions were extracted with methylene chloride. The solvent was dried with sodium sulfate and removed under reduced pressure to yield 50 mg of product a colorless oil: $^1$H NMR (300 MHz, CDCl$_3$) 3.25–3.42 (m, 4H), 2.72 (s, 3H), 1.23 (t, 3H), 1.17 (t, 3H); mass spectroscopy: CIMS (NH$_3$) M/Z, 180 (M$^{+1}$); IR (neat): 2954, 1668, 1436, 1400, 1317, 1136, 1113, 747 cm$^{-1}$.

EXAMPLE 4
Evaluation of DETC-Me Sulfoxide and DDTC-Me Sulfoxide as In Vitro Inhibitors of Rat Liver Low Km Aldehyde Dehydrogenase To determine whether a compound of formula (I) can inhibit low Km aldehyde dehydrogenase, an amount of the compound is added to isolated mitochondria. To prepare isolated mitochondria, male Sprague-Dawley derived rats weighing 200–400 g were anesthetized with carbon dioxide and then decapitated. The livers from untreated rats were homogenized in 0.25 M sucrose and differential centrifugation carried out to isolate the mitochondrial fraction. The mitochondria were solubilized with sodium deoxycholate, and mitochondrial low Km ALDH activity determined by the method of S.O.C. Tottmar et al., *Biochem. J.*, 135,577 (1973).

Mitochondria were isolated from the liver of untreated rats and resuspended in 0.1 M phosphate buffer pH=7.4). Incubations contained 2 mg of mitochondrial protein, to which was added DETC-Me SO at 0.2 μM, 2.0 μM, 20 μM or 200 μM, or DDTC-Me SO at 0.5 μM, 2.5 μM, 10 μM, 25 μM, 50 μM or 100 μM. The DETC-Me SO or DDTC-Me SO was dissolved in ethanol and the incubations carried out for one hour. Control incubations contained ethanol alone.

At the end of the incubation, the mitochondria were isolated by centrifugation, resuspended in 0.25 M sucrose buffer and solubilized with deoxycholate. Low Km ALDH activity was determined by the method of S.O.C. Tottmar et al., cited above.

As the concentration of the DETC-Me SO is increased, inhibition of rat liver mitochondrial low Km ALDH also was increased until maximal inhibition of ALDH was reached. The concentration of DETC-Me SO required for 50% inhibition of the rat liver mitochondrial low Km ALDH was approximately 750 nM. For comparative purposes, 200 μM S-methyl-N, N-diethylthiocarbamate produced only an 8% inhibition. In both experiments, incubations were carried out for one hour. The concentration of DDTC-Me SO required for 50% inhibition is about 15 μM. It is concluded that DETC-Me SO is an extremely potent inhibitor of rat liver mitochondrial low Km ALDH in vitro.

EXAMPLE 5
Liver Aldehyde Dehydrogenase Determined In Vivo

To determine if a compound of formula (I) can inhibit aldehyde dehydrogenase activity in vivo, doses of DETC-Me SO (1.3 mg/kg, 2.6 mg/kg, 5.2 mg/kg, 10.3 mg/kg and 20.6 mg/kg), were administered to male Sprague Dawley derived rats weighing 200–400 g. The rats were bred from a resident colony maintained in the Animal Care Unit at the University of Kansas. Rats were maintained on a 12-hour light-dark cycle with access to food and water ad lib until the night before an experiment, at which time food was removed. Animals were fasted for 12 hours prior to drug administration.

All experiments were carried out in the morning. Rats were treated with the doses of DETC-Me SO or DETC-Me described above, which were dissolved in polyethylene glycol 200. Eight hours later, the rats were anesthetized with carbon dioxide and then decapitated. The liver was quickly removed and the low Km aldehyde dehydrogenase determined. Control rats were treated with corn oil vehicle only, and each control data point also represents an average of four rats.

The liver from drug-treated and control rats was homogenized in 0.25 M sucrose and differential centrifugation was carried out to isolate the mitochondrial fraction. The mitochondria were solubilized with sodium deoxycholate, and mitochondrial low Km and total (high and low) aldehyde dehydrogenase activity determined by the method of S.O.C. Tottmar et al., cited above.

As the administered dose of DETC-Me SO is increased, there was a greater degree of rat liver mitochondrial low Km ALDH inhibition. The dose of DETC-Me SO required to inhibit 50% of the low Km ALDH is 3.6 mg/kg intraperitoneal (IP). For comparative purposes, DETC-Me required a dose of 6.5 mg/kg IP to produce a comparable degree of low Km ALDH inhibition. Furthermore, the dose of disulfiram which inhibited 50% of the rat liver mitochondrial low Km ALDH is 56.2 mg/kg IP. Therefore, DETC-Me SO is substantially more potent as a rat liver mitochondrial low Km ALDH inhibitor than disulfiram.

EXAMPLE 6
Plasma Acetaldehyde Determination

Rats maintained as described in Ex. 4, fasted for 18 hours, were given 10.3 mg/kg of the DETC-Me SO intraperitoneally, dissolved in polythylene glycol 200 and then challenged eight hours later with a dose of ethanol (1 g/kg; 20% v/v) also administered intraperitoneally. The rats were anesthetized with phenobarbital 30 minutes after alcohol administration and blood was taken by aortic puncture, being drawn into a heparinized syringe. Plasma acetaldehyde was determined by the method of C.O.P. Eriksson er al., *Anal. Biochem.*, 80, 116 (1977). Plasma concentrations were determined based on a standard curve obtained with known concentrations of acetaldehyde. Control rats were treated with 1 ml/kg of polyethylene glycol 200.

A large increase in plasma acetaldehyde was detected after the IP administration of 10.3 mg/kg of S-methyl-N, N-diethylthiolcarbamate sulfoxide dissolved in polyethylene glycol 200, to male rats which were then challenged with 1 g/kg ethanol (20% v/v) IP 30 minutes later. Plasma acetaldehyde increased to approximately 900 μM. Control rats received polyethylene glycol 200 only, and were then challenged with 1 g/kg ethanol IP. In these controls, plasma acetaldehyde was barely detectable. It is concluded that DETC-Me SO can markedly increase plasma acetaldehyde after an ethanol challenge. The increase in acetaldehyde is believed to be responsible for initiating the disulfiram-ethanol reaction, which deters further alcohol consumption.

EXAMPLE 7
Inhibition of Aldehyde Dehydrogenase and Succinic Semi-Aldehyde Dehydrogenase To test whether the protective effect of DETC-MeSO in hyperbaric O$_2$-induced convulsions in mice could be due to inhibition of succinic semi-aldehyde dehydrogenase (SSA DH), mechanistically related to ALDH$_2$, the sensitivity of SSA DH to inactivation by DETC-MeSO was determined. Potentially, inhibition of SSA DH in brain could offset the build up of ammonia known to occur and produce more GABA. In vitro both ALDH$_2$ and SSA DH are inactivated by DETC-MeSO at 47 M-1 s-1 and 300 M-1 s-1, respectively. However, in vivo, only ALDH is sensitive to inactivation by DETC-MeSO (84% inhibition of mouse liver enzyme by 2.6 mg/kg DETC-MeSO i.p.); with no effect on the levels of brain or liver SSA DH (up to 100 mg/kg i.p.).

EXAMPLE 8
In Vivo Properties of DETC-MeSO

DETC-MeSO has a highly selective and rapid carbamoylating agent for free thiol groups. Under physiological conditions (37° C.; pH7) it carbamoylates the sulfhydryl group of glutathione (GSH) at a rate of $10\ M^{-1}\ s^{-1}$. This rate of reaction was approximately an order of magnitude faster than that of the more familiar α-haloketone functionality. Moreover, the carbamoylated glutathione was relatively stable under physiological conditions and was not itself a reactive molecule without oxidative activation. The sulfenic acid of methyl mercaptan, also produced in the reaction of DETC-MeSO with GSH, can be reduced to methyl mercaptan and water by the combined action of glutathione, NADH, glutathione peroxidase, and glutathione reductase, at the expense of reduced pyridine nucleotide. Inactivation of aldehyde dehydrogenase (ALDH) has indicated that only approximately 0.5 moles of carbamoylation per mole of active sites is required for inactivation ("half-of-sites" reactivity).

At a dose of 5.2 mg/kg i.p. in mice, DETC-MeSO achieved 80% inactivation of ALDH in 1 hour. Since the rate for enzyme inactivation is $40\ M^{-1}\ s^{-1}$ under physiological conditions, the effective concentration of DETC-MeSO at its site of action in vivo is about 11 $\mu$M. If the DETC-MeSO were simply evenly dispersed throughout the animal, its concentration would be approximately 32 $\mu$M. This would imply a very effective delivery and utilization of DETC-MeSO, however, it ignores the rather high concentrations of GSH that are present in blood, 1 mM, less than 5% of DETC-MeSO would remain after 5 minutes. In liver, less than 3% of DETC-MeSO would remain after only one minute. GSH actually mediates the effect of DETC-MeSO. Carbamoylated GSH inactivates ALDH and/or blocks glutamate binding to synaptic membranes nearly as effectively as DETC-MeSO (in vivo, but not in vitro), when the former is injected i.v. or i.p. in mice. However, to complete this cycle the carbamoylated GSH must be activated by oxidation. This may be accomplished via glutathione peroxidase at the expense of intracellular hydrogen peroxide.

To separate the effect of carbamoylating agents on ALDH and the glutamate receptors, the size of the substituents on the nitrogen of the carbamoyl group is varied. Initially the methyl sulfoxide part of the molecule is maintained and the effectiveness of derivatives is tested in vitro for potential intrinsic differences, prior to testing their effectiveness in vivo. Different results in the relative effectiveness of these agents in vitro and in vivo against the ALDH and glutamate receptors are not unexpected due to potential differences in transport and metabolism of these compounds before or after carbamoylation of GSH.

Initially a series of symmetrically substituted compounds are examined in which the nitrogen is N,N-dimethyl, di-n-propyl, or di-n-butyl. The synthetic scheme currently employed for DETC-MeSO readily lends itself to preparation of these derivatives and many others, in that the amine can be condensed with carbon oxysulfide and methyl iodide, followed by oxidation of the thio ester with sodium metaperiodate.

EXAMPLE 9
Bioactivity of DETC-MeSO

The following test could be used to test the anti-craving effect of DETC-MeSO and other compounds of the invention. Syrian hamsters are employed in methods similar to those of Keung and Valee, *Biochemistry*, 90, 10008 (1993). Dose response studies for DETC-MeSO on liver low Km mitochondrial aldehyde dehydrogenase (ALDH) are conducted first to establish a dose for DETC-MeSO. The doses of DETC-MeSO to be used in these studies are, for example, 2.6, 5.2, 10.4 and 20.8 mg/kg given ip in PEG 200.

Hamsters (20 adult hamsters weighing 130–135 g) are preconditioned to drink 25% alcohol v/v by placing them in metabolic cages individually with free access to 25% alcohol v/v. Those hamsters that consume more than 8 ml/day are selected for the study. It is anticipated approximately 70–90% of the hamsters will be preconditioned to consume alcohol.

From this preconditioned group, selected hamsters are divided in two groups. A control group, which receives PEG 200 and a DETC-MeSO-treated group. The dose of drug to be administered is determined from the dose-response studies. Each hamster is placed in a metabolic cage. Two drinking fluids are supplied for each hamster. One being filtered water and the other 25% v/v alcohol. The position of each the two drinking bottles on each cage is alternated daily to prevent development of positional preference. Fluid intake is measured at 9:00 A.M. each day. Total alcohol consumed will be calculated and drug efficacy determined.

To determine if the drugs of interest are useful inhibiting alcohol withdrawal-induced seizures, male C57BL mice (20–24 g) are employed. The mice are housed individually with wood bedding. Lighting is on a 12-hr cycle. Mice (n=20) are given liquid diet containing 7% (v/v) ethanol and vitamin C supplement for 7 days. Every 24-hr the amount of ethanol consumed is measured and replaced with fresh ethanol-containing diet. Withdrawal is initiated at 7:00 A.M. of 8th day by replacing the ethanol-containing diet with ethanol-free diet. Mice are divided into two groups of ten each. One group (n=10) is treated with DETC-MeSO. The other group (n=10) which serve as controls is given PEG-200.

Two doses of DETC-MeSO are used, 2 mg/kg or 10.4 g/kg, which are administered (intraperitoneally) daily for three days during the course of alcohol withdrawal.

Handling-induced withdrawal seizures are rated on a 0–4 scale as described by Grant et al. (1994). The mice are picked up by the tail and are rated as follows: 0, corresponds to little or no reaction; 1, corresponds to a mild reaction; 2, corresponds to initial hyperactivity escalating into a clonic-tonic seizure upon handling; 4, corresponds to death as a result of seizure. Two investigators, blind to the drug conditions rate the mice for seizure severity at 2-hr intervals for the first 6-hr of withdrawal (2, 4, and 6 hr into withdrawal), then every hour until 11 hr of withdrawal (7, 8, 9, 10 and 11 hr of withdrawal). DETC-MeSO is then evaluated for its effect in preventing alcohol-withdrawal seizures.

EXAMPLE 10
General Procedure for Preparation of Compounds of Formula $(R^1)(R^2)$ NC(=O) $SCH_3$ Equimolar amounts of amine $[(R^1)(R^2)NH]$ and triethyl amine are combined in methylene chloride so that the concentration of each amine is approxmately 0.3M. The solution is cooled to −78° C. under an inert atmosphere, and carbonyl sulfide (g) is bubbled through the mixture. After carbonyl sulfide addition is terminated, the resulting solution is stirred for 30 minutes. Two equivalents of methyl iodide are added dropwise from an addition funnel at approximately 1 drop/second. After approximately 1.2 hours, the solution is condensed using a rotary evaporator until a precipitate appears. Diethyl ether is added to precipitate the salt and the mixture is filtered [CAUTION: the precipate should be redissolved in water and disposed of as hazardous waste]. The combined ether washes are condensed using a rotary evaporator to give the compound of formula $(R^1)(R^2)$ $NC(=O)SCH_3$.

EXAMPLE 11
General Procedure for Preparation of Compounds of Formula $(R^1)(R^2) NC(=O) S(=O)CH_3$ Sodium periodate (8.3 g) is dissolved in 180 mL of water and added to the compound from Example 10 (5 g) in a 1 L round-bottom flask, and the solution is cooled to 4° C. under an inert atmosphere. The flask is wrapped in aluminum foil to shield light. When trace amounts of the sulfone are apparent by HPLC or TLC (24–72 hours), the reaction mixture is subjected to reverse phase medium pressure liquid chromatography (C-18, see Example 1 and 2)) or flash chromatography (silica gel), with acetonitrile as the eluent to, give the compound of formula $(R^1)(R^2) NC(=O)S(=O)CH_3$.

Using the general procedures of Examples 10 and 11, the following compounds were prepared: S-methyl N,N-dimethylthiolcarbamate sulfoxide (DMTC-SO); S-methyl N,N-diethylthiolcarbamate sulfoxide (DETC-SO); S-methyl N,N-dipropylthiolcarbamate sulfoxide (DPTC-SO); and S-methyl N,N-dibutylthiolcarbamate sulfoxide (DBTC-SO).

General Materials and Methods for Examples 12 and 13

Animals—Male Swiss Webster mice (20–30 g) or male Sprague-Dawley rats (250–300 g) were used. All experiments that employed animals were conducted in strict compliance with the NIH guidelines on animal use and institutional regulations concerning animal experimentation. Animals were exposed to hyperbaric oxygen in a specially designed pressure chamber as previously describe (M. D. Faiman et al., *Biochem. Pharmacol.*, 20, 3049–3067 (1971); M. D. Faiman et al., *Aerosp. Med.*, 45, 29032 (1974)). The time to first clonic-tonic seizure after brining animals to a final pressure of five atmospheres of 100% oxygen or after intraperitoneal injection of convulsants was noted by criteria outlined previously (M. D. Faiman et al. (1971), supra; M. D. Faiman et al. (1974), supra). Unless otherwise specified, the ability of DETC-MeSO to prevent seizures was tested by intraperitoneal injection of 5.2 mg/kg of DETC-MeSO 1–2 hours prior to bringing the animal to a final pressure of 5 atmospheres of 100% oxygen or intraperitoneal injection of N-methyl-D-aspartate (NMDA) (125 mg/kg) or L-methionine sulfoximine (MetSOX) (250 mg/kg). Evaluation of the statistics for whole animal experiments or for changes in brain glutamate binding after administration of DETC-MeSO was conducted by use of the program Graph-PAD InStat from Graph PAD Software (San Diego, Calif.).

Binding Studies—Synaptic membranes (100 μg protein) were isolated (Y. H. Lee et al., *J. Neurosci. Res.*, 40, 797–806 (1995)) form whole brain homogenate of male Swiss Webster mice and were incubated in 0.1 mM L-glutamate for 30 minutes at 25° C. After addition of 50 nM of [$^3$H]glutamate, incubation was continued for an additional 45 minutes. Reactions were terminated by centrifugation at 4° C. to separate membrane-bound from free radioactivity. Nonspecific binding (radioactivity bound in the presence of 0.5 mM unlabeled glutamate) averages 20–30% of total radioactivity bound. The rate (k) and maximum percent blockage of glutamate binding (M) by DETC-MeSO (I) during the incubation time (t) was determined by fitting the equation [% inhibition]=$M(1-e^{-kIt})$ to these day by use of the program Grafit (Erithicus Software Ltd.). This equation was derived for first-order inactivation by a group specific reagent that gives a partial effect. If "A" is the percent of binding activity that remains after extensive exposure (t=∞) of the receptor to excess DETC-MeSO, then $M=100-A)e^{-kIt}+A$; substituting (100−M) for "A" and [100−% inhibition] for "a" in this equation gives the one employed for purposes of data analyses. The maximum percent blockage of glutamate binding (M) observed did not depend on the concentration of glutamate employed in binding experiments, such that the modified receptors appeared to be "non-competitively" inhibited (independent of whether DETC-MeSO was still present or absent at the time that glutamate binding was assayed). A second equation was employed in the analysis of binding data that defines partial, irreversible inactivation of two distinct groups of receptors: [% inhibition]=$M_1(1-e^{-k_1 I T})+M_2(1-e^{-k_2 I T})$, where $M_1$ and $M_2$ are the maximum amount of inhibition obtained for complete modification of each receptor population and $k_1$ and $k_2$ are the rate constants for these modifications, respectively.

Reagents—DETC-MeSO was synthesized by the method of Hart and Faiman (B. W. Hart et al., *Biochem. Pharmacol.*, 43, 403–406 (1992). Carbamoylated glutathione, S-(N,N-diethylcarbamoyl)glutathione (DETC-GS), was prepared essentially as described by Jin et al. (L. Jin, supra). The structures and purity of DETC-MeSO and DETC-GS were confirmed by 300 MHz NMR and FAB-tandem mass spectrometry. A QE300 NMR spectrometer (General Electric, Fremont, Calif.) and Autospec-Q Tandem Hybrid mass spectrometer (Fiscons/VG Analytical Limited, Manchester, England) were employed for these analyses. Liver aldehyde dehydrogenase was extracted and assayed as previously described (B. W. Hart et al., supra). MetSOX, monosodium L-glutamate, glycine, glutathione, and NMDA were purchased from Sigma Chemical Company (St. Louis, Mo.). L-[3-$^3$H]Glutamate (46 Ci/mmol) was obtained from Amersham Life Science (Buckinghamshire, England).

EXAMPLE 12
DETC-MeSO Effects on Brain Glutamate Receptors in Vitro

Figure 2:
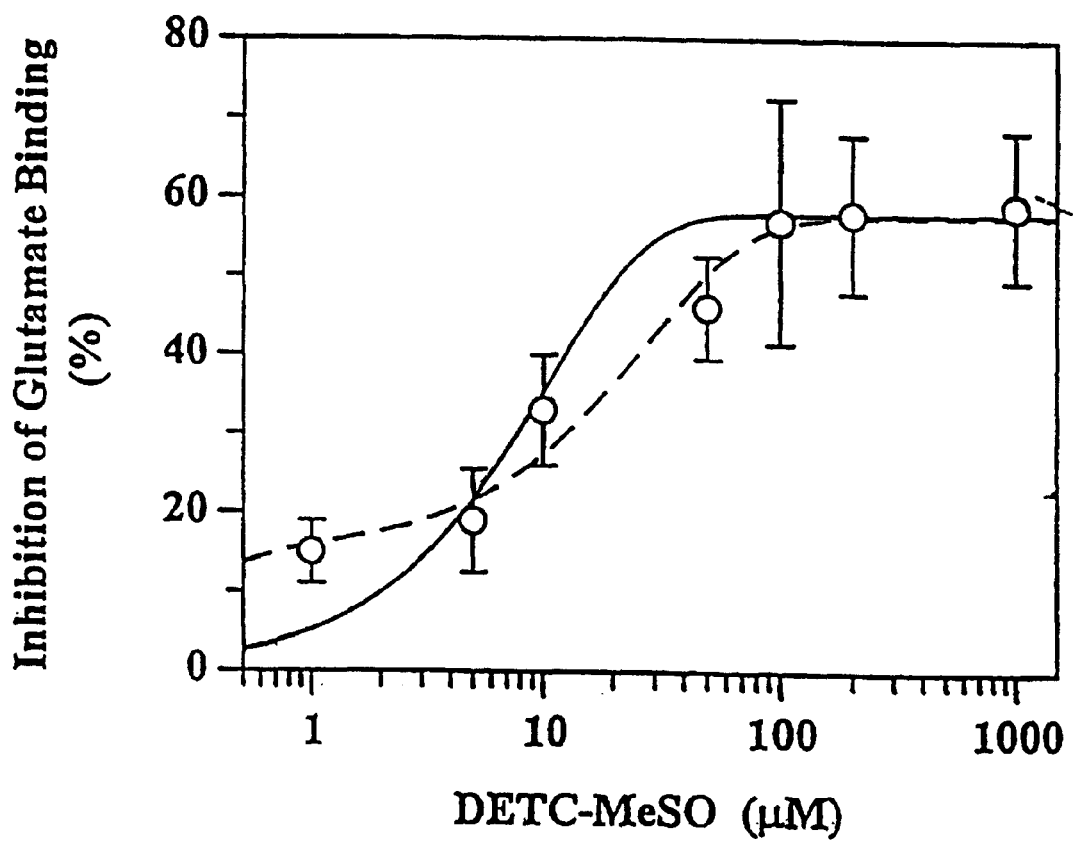
FIG. 2 illustrates inhibition of glutamate binding to brain synaptic membranes in vitro by DETC-MeSO.

Treatment of synaptic membrane preparations (Y.-H. Lee et al., supra) from the brains of mice with DETC-MeSO, resulted in a time-dependent, partial, and irreversible loss of their ability to bind glutamate (FIG. 2). Six determinations of the effect of DETC-MeSO were made at each concentration tested (1, 5, 10, 50, 100, 200, and 1000 μM) and the average value is shown with error bars for one standard deviation. The values for M and k obtained when a single exponential was fit to data were 58±7% and 25±10 $M^{-1} s^{-1}$, respectively, and the line calculated by use of these values is shown (-). A dashed line (- - -) that was calculated for a double exponential equation fit to data with nominal values of $M_1=15\%$, $M_2=43\%$, $k_1=900$ $M^{-1} s^{-1}$, and $k_2=8$ $M^{-1} s^{-1}$ is also shown. Inhibition of glutamate binding appears to depend on modification of more than one population of glutamate receptor, each with distinct kinetics. Although a better fit of these data could be obtained by use of a double exponential equation, a unique fit of this equation to these data could not be obtained, due to the larger number of independent parameters involved. However, a nominal fit of these data indicated that about one-fourth of the total inhibition ($M_1=15\%$) occurs at a much faster rate ($k_1=900$ $M^{-1}$ $s^{-1}$), than the rate ($k_2=8$ $M^{-1}$ $s^{-1}$) associated with inhibition of the remainder ($M_2=43\%$)(FIG. 2). Since the effect of DETC-MeSO on either receptor population is irreversible, glutamate receptor blockage in vivo can be easily determined.

EXAMPLE 13
DETC-MeSO Effects on Brain Glutamate Receptors in Vivo

Figure 3:
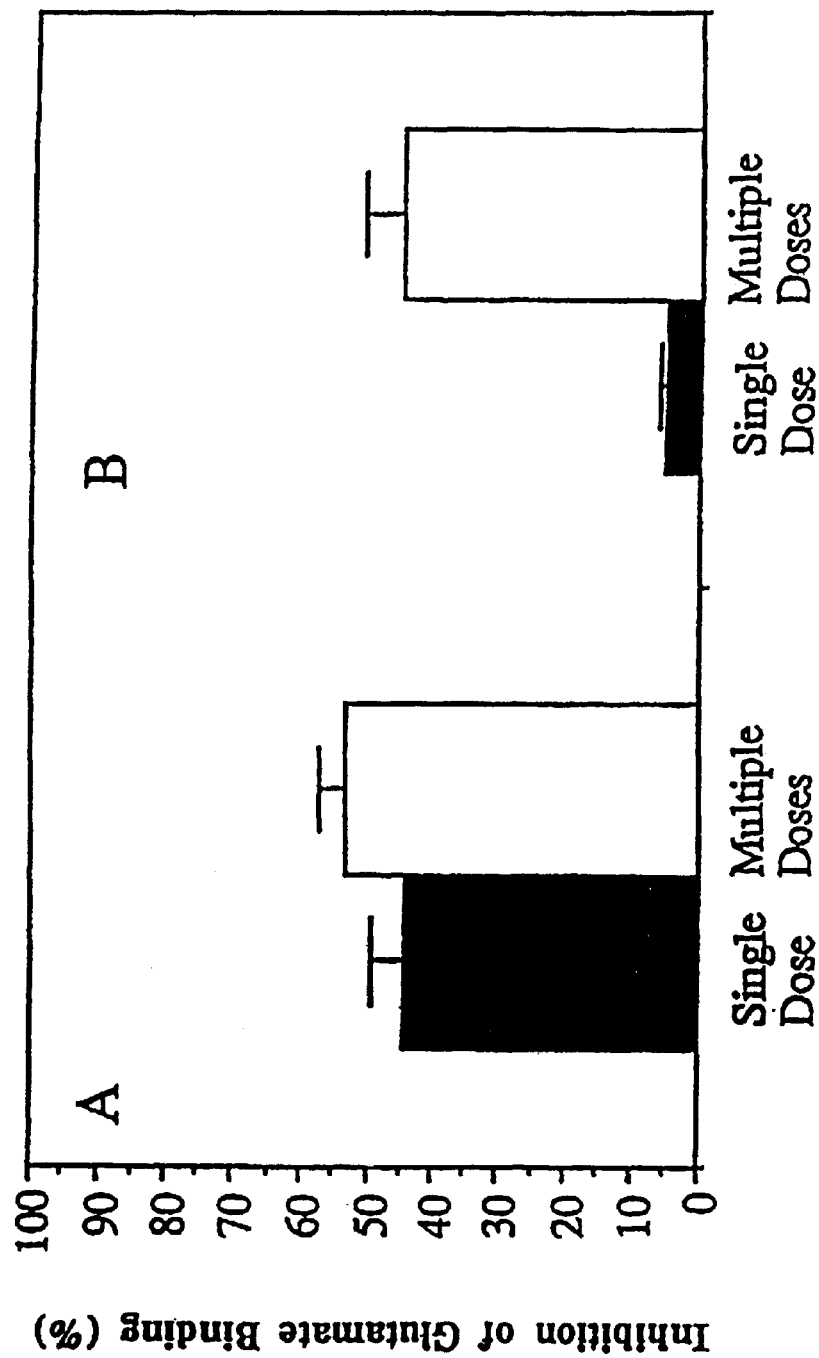
FIG. 3 illustrates glutamate binding to synaptic membranes isolated from Swiss Webster male mice killed 2 hours (A) or 24 hours (B) post-injection of a single administration of DETC-MeSO (5.2 mg/kg, i.p.) or after the last of seven daily injections.

Synaptic membranes were prepared from the brains of mice injected with DETC-MeSO (5.2 mg/kg, i.p.). The ability of synaptic membrane preparations isolated from DETC-MeSO-treated mice to bind glutamate was compared with similar preparations isolated from control animals. FIG. 3 (A) illustrates the results obtained from synaptic membranes prepared from brains of mice killed two hours after a single dose of DETC-MeSO, or two hours after the last injection of multiple consecutive doses (5.2 mg/kg, i.p., daily for seven days). Either single or multiple dosing with DETC-MeSO reduced the capacity of synaptic membranes to bind glutamate by approximately 50%, the maximum effect obtained in vitro (FIG. 3). Each bar represents the average of results obtained from four animals and the error bars are for one standard deviation.

For brain synaptic membrane preparations isolated from mice killed 24 hours after a single dose of DETC-MeSO, less inhibition of glutamate binding was found (FIG. 3B). By contrast, for brain synaptic membrane preparations isolated from mice killed 24 hours after the last dose of seven daily consecutive doses, similar inhibition of glutamate binding to that seen 2 hours post-injection of DETC-MESO (FIG. 3). The results obtained for the group that received a single dose of DETC-MeSO and were sacrificed after 2 hours were significantly different from the group that received a single dose and were sacrificed after 24 hours (Bonferroni's p<0.01 determined by ANOVA). Comparison of the singly dosed group that was sacrificed after 2 hours with the multiple dosed groups that were sacrificed after 2 hours or 24 hours did not show statistical significance from each other by the same criteria.

Figure 4:
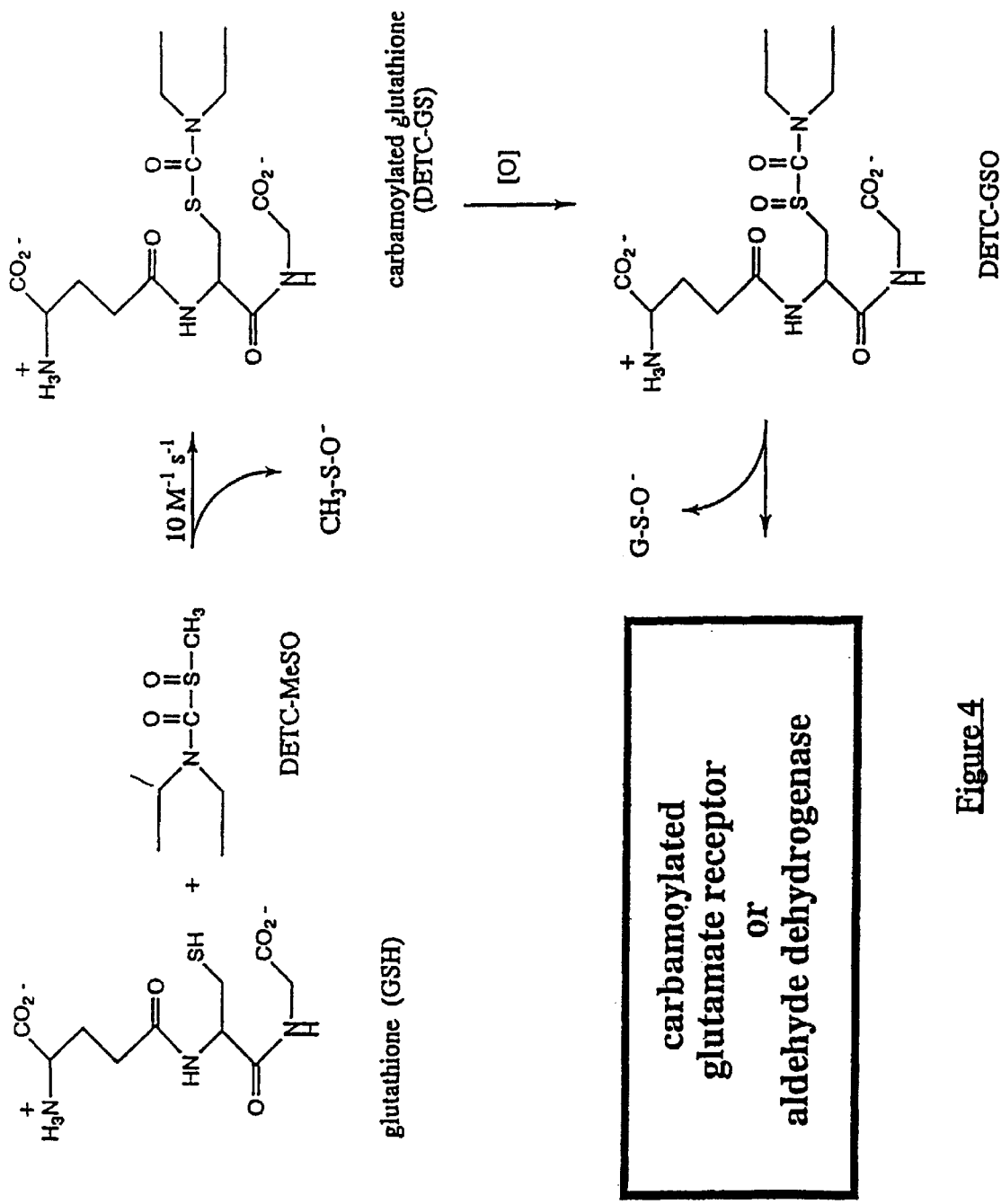
FIG. 4 illustrates interconversion of DETC-MeSO, DETC-GS, DETC-GSO, and the carbamoylation of glutamate receptors.

It is hard to reconcile the ability of DETC-MeSO to carbamoylate brain glutamate receptors with its extreme lability in vivo. DETC-MeSO rapidly and selectively carbamoylates and the sulfhydryl of glutathione (GSH) in vitro ($10\ M^{-1}s^{-1}$ at $37°$ C., pH 7), and since the concentration of GSH in vitro is high (1–6 mM) (D. W. Potter et al., *Toxicol. Appl. Pharmacol.*, 120, 186–192 (1993)), DETC-MeSO will rapidly be converted (>95% within 5 minutes) to N,N-diethyl-S-carbamoyl-glutathione (DETC-GS, FIG. 4). DETC-GS has been detected in the bile of mice treated with disulfiram (L. Jin, supra). Unlike DETC-MeSO, DETC-GS is not reactive and does not carbamoylate sulfhydryl groups (L. Jin, supra). Although DETC-GS reversibly blocked glutamate binding to synaptic membrane preparations from mouse brain (data not shown), a time-dependent, irreversible blockage of the glutamate receptor, like that observed with DETC-MeSO, was not obtained.

If the effect of DETC-MeSO on glutamate receptors in vivo is mediated by glutathione, then the carbamoylated glutathione requires activation. Glutathione (GSH), oxidized glutathione (GSSG), and DETC-GS reversibly blocked glutamate binding to mouse synaptic membrane preparations (data not shown). However, when the membranes were washed after exposure to GSH, GSSG, or DETC-GS, inhibition was reversed, unlike the effect by DETC-MeSO. Oxidation of the sulfur of DETC-GS to a sulfoxide would make it reactive toward sulfhydryl groups (A. Madan et al., supra), similar in chemistry to DETC-MeSO, and potentially capable of irreversible inhibition of glutamate receptors in vivo.

Carbamoylated glutathione and DETC-MeSO had the same effect in vivo, despite the fact that they had different effects on glutamate receptors in vitro. Intravenous administration of an equimolar concentration of DETC-GS or DETC-MeSO (30 μmol/kg) to mice resulted in a comparable degree of irreversible brain glutamate receptor blockage (26.9±4.3 and 38.2±1.6%, respectively) or liver aldehyde dehydrogenase inhibition (30.1±1.0 or 44.9±1.0%, respectively). Since DETC-GS reversibly blocked glutamate binding to synaptic membranes in vitro (i.e., the inhibition can be reversed by washing the membranes to remove DETC-GS), but in vivo both DETC-MeSO and DETC-GS irreversibly blocked glutamate binding, and DETC-GS has no effect on aldehyde dehydrogenase in vitro (reversible or irreversible), it is suggested that DETC-GS is activated by oxidation in vivo (DETC-GSO, FIG. 4).

EXAMPLE 14

Neuroprotective Effects of DETC-MeSO

To test whether carbamoylation of glutamate receptors might prevent seizures caused by glutamate agonists, the effect of DETC-MeSO on seizures induced by glutamate analogs was examined.

TABLE 1

| Treatment | Control Animals mean time to seizure (min) | DETC-MeSO Treated[b] mean time to seizure (min) |
|---|---|---|
| NMDA | 16 ± 3 | >120[a] |
| (125 mg/kg, mice) | (5/8)[a] | (0/6)[a] |
| MetSOX | 127 ± 24 | 307 ± 60 |
| (250 mg/kg, mice) | (8/8) | (6/8)[a] |
| MetSOX | 136 ± 6 | 318 ± 60 |
| (250 mg/kg, rats) | (4/4) | (4/4) |
| 5 ATA[c] $O_2$ | 24 ± 3 | >60[a] |
| (mice) | (7/7) | (0/5)[a] |

[a]The mean values for the time to the first clonic-tonic seizure are reported ± standard error. Immediately below this value in brackets is the number of animals that exhibited the effect divided by the total number of animals in that group (number of animals to which value applies/total number of animals in the group). Comparison of the means for control (untreated) and DETC-MeSO-treatedanimals by a two tailed t-test gave p < 0.001. In the case of NMDA treatment, three of the eight animals in the control group failed to exhibit any seizures, even after a second injection of NMDA. Resistance to NMDA-induced seizures appears to be due to $P_{450}$-mediated metabolism of this glutamate analog, based on the ability of N-benzylimidazole, a $P_{450}$ inhibitor, to produce sensitivityin NMDA-resistant animals. None of the animals in the DETC-MeSO-treated group (six out of six animals exhibited any NMDA-induced seizures for the duration of the observation period (2 hours). In the case of MetSOX treatment, two out of eight animals in the DETC-MeSO-treated group remained free of seizures for the period of observation (six hours). In the case of hyperbaric oxygen exposure (5 ATA $O_2$),all of the animals in the DETC-MeSO-treated group (five out of five animals) remained free of seizures for the period of observation (one hour).
[b]DETC-MeSO was administered at a dose of 5.2 mg/kg by intraperitoneal (i.p.) injection 1–2 hours prior to exposure to hyperbaric oxygen, NMDA, or MetSOX.
[c]Mice were exposed to five atmospheres absolute (ATA) of 100% oxygen in a pressure chamber for 60 minutes, then depressurized.

Treatment of mice with DETC-MeSO prior to administration of the glutamate analog N-methyl-D-aspartate (NMDA) (125 mg/kg, i.p.) prevented seizures that result from NMDA administration alone (Table 1). Similarly, DETC-MeSO administered to mice or rats prior to injection of the glutamate analog methionine sulfoximine (MetSOX) more than doubled the time that the animals remain free of seizures (Table 1).

It has been shown that glutamate is released by rat hippocampal (brain) slices subjected to oxidative stress (D. E. Pellegrini-Giampietro et al., *J. Neurosci.*, 10, 1035–1041 (1990)). Therefore, the effect of DETC-MeSO on oxygen-induced seizures was investigated. Administration of DETC-MeSO (5.2 mg/kg, i.p.) to mice 2 hours before exposure to 5 atmospheres of 100% oxygen, prevented the seizures that occurred after 24 minutes in control animals (Table 1).

EXAMPLE 15
Effect of DETC-MeSO on NMDA and non-NmDA Subtypes of Brain Glutamate Receptors NMDA is a selective agonist for a major subtype of ionotropic (calcium ion channel-linked) glutamate receptor (N. Burnashev, *Cell. Physiol. Biochem.*, 3, 318–331 (1993)). As determined in the results illustrated in FIGS. 2 and 3, the effect of DETC-MeSO on glutamate binding to synaptic membrane preparations is not a measure of DETC-MeSO's modification of this receptor subtype. Although up to 34% of the total glutamate binding capacity of synaptic membranes is attributable to NMDA receptors (M. Cincotta et al., *Anal. Biochem.*, 177, 150–155 (1989)), the effect of glutamate on these receptors is dependent on glycine (D. W. Bonhaus, *Mol. Pharmacol.* 36, 273–279 (1989)), that was not included in the studies presented in FIGS. 2 and 3. Under the conditions of these experiments,. NMDA does not block glutamate binding to synaptic membrane preparations. When these binding experiments were repeated in the presence of glycine (0.1 mM), reversible blockage of glutamate binding to mouse brain synaptic membrane preparations by NMDA (0.5 mM, 32±2% blockage) and irreversible blockage by DETC-MeSO (0.1 mM, 48±3% blockage) was observed. The similar degree of inhibition observed by DETC-MeSO in the presence and absence of glycine [48 and 53% (FIG. 2), respectively] indicates that both NMDA and non-NMDA glutamate receptor subtypes are affected to a similar extent by carbamoylation.

EXAMPLE 16

Figure 5:
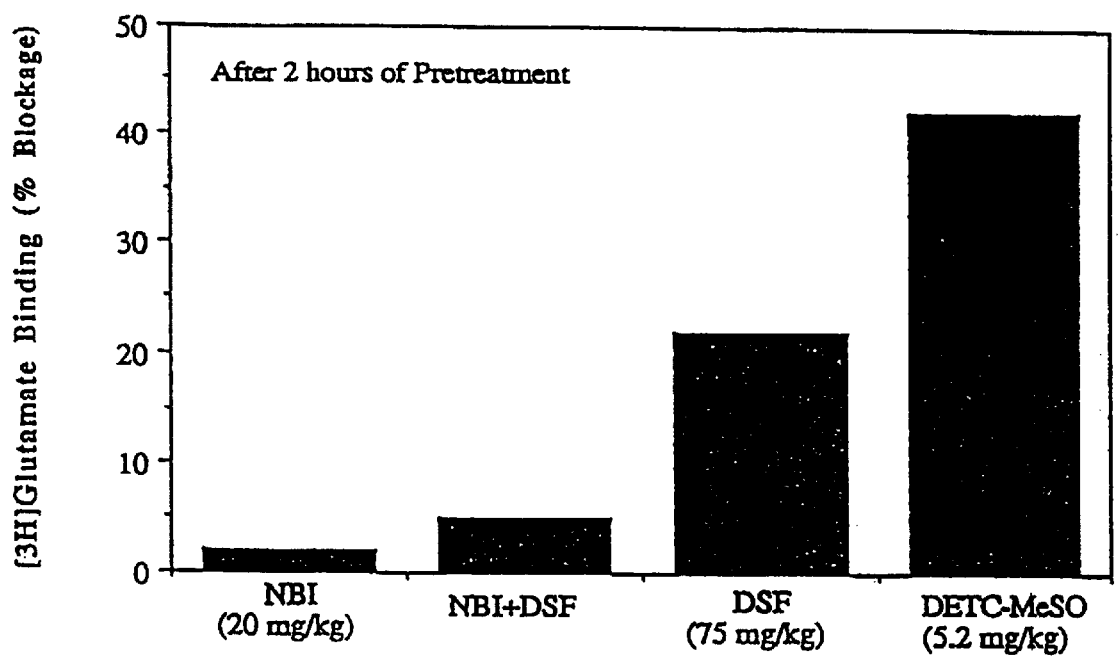
FIG. 5 illustrates [$^3$H]glutamate binding to mouse brain P-2 Pellet Preparation after 2 hours of pretreatment with DSF or DETC-MeSO.

Using a protocol similar to that described in Example 12, the [$^3$H]glutamate binding to mouse brain P-2 pellet preparation was determined, following treatment with disulfiram (DSF), DETC-MeSO, or a combination of N-butyl imidazole(NBI) and disulfiram. As shown in FIG. 5, the effects of disulfiram can be blocked by NBI, which is known to inhibit the conversion of disulfiram to DETC-MeSO. This shows that formation of DETC-MeSO by metabolism of disulfiram is required for activity in vivo.

EXAMPLE 17

Figure 6:
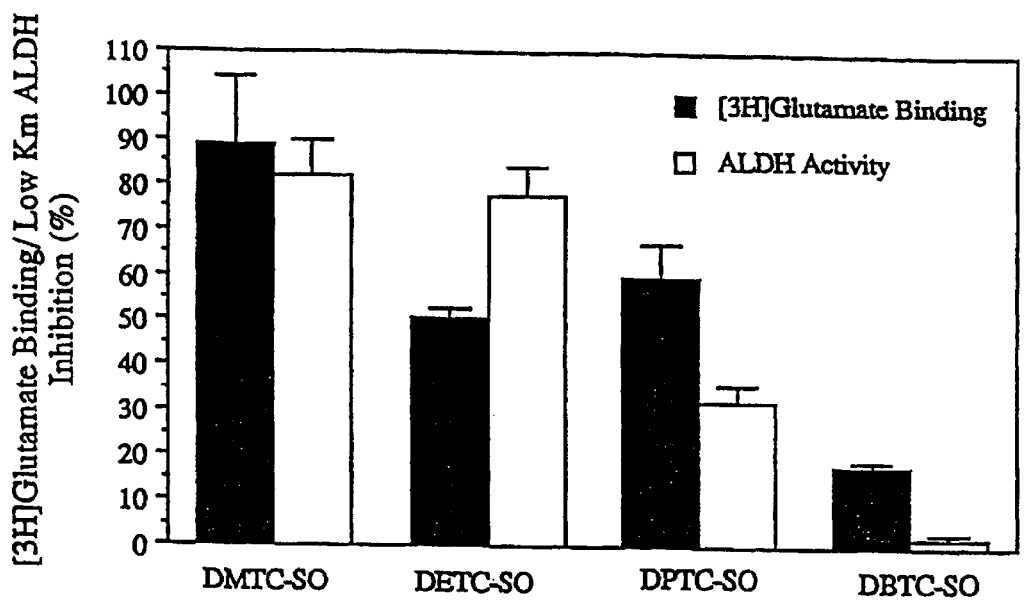
FIG. 6 illustrates [$^3$H]glutamate binding to mouse brain synaptic membrane and low liver Km ALDH activity after treatment with 30 micromolar solutions of identified compounds.

Using a protocol similar to that described in Example 13, the [$^3$H]glutamate binding to mouse brain synaptic membrane, and the low liver Km ALDH activity was determined following treatment with 30 micromolar solutions of representative compounds. Results are shown in FIG. 6. This shows that the effects on aldehyde dehydrogenase and the glutamate receptor can be distinguished from one another.

EXAMPLE 18

Figure 7:
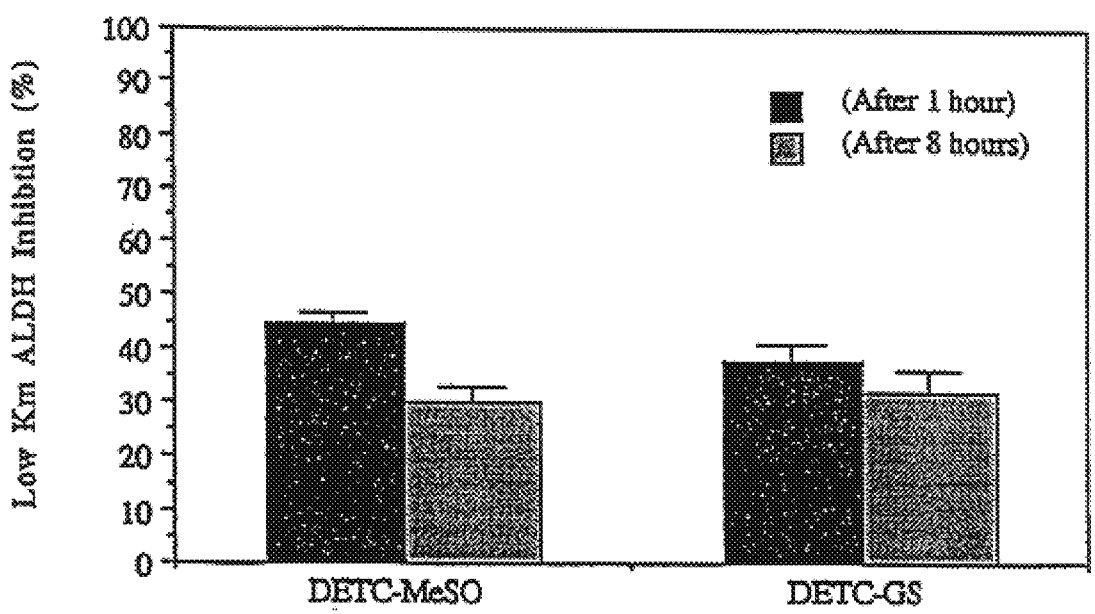
FIG. 7 illustrates mouse liver low Km ALDH inhibition by DETC-MeSO/DETC-GS (30 micromolar, i.v.)
Figure 8:
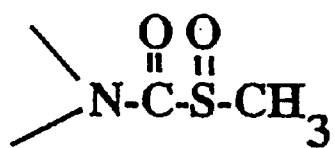
FIG. 8 shows the structure of representative compounds useful for practicing the methods of the invention.
Figure 8:
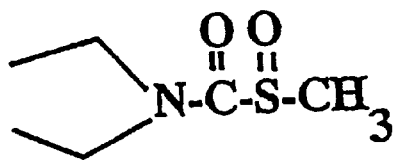
Figure 8:
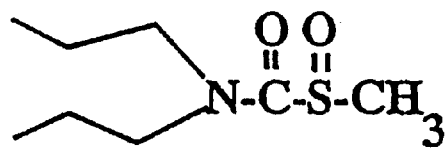
Figure 8:
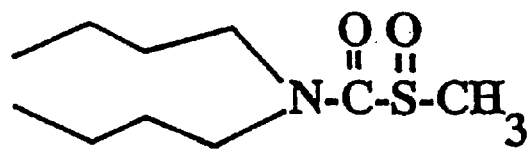

Using a protocol similar to that described in Example 13, the mouse liver low Km ALDH inhibition by DETC-MeSO and DETC-GS (30 micromolar, i.v.) was determined. Results are shown in FIG. 7. This shows that DETC-GS has the same effect as DETC-MeSO in vivo, and is an intermediate in this effect.

The invention has been described with reference to various specific preferred embodiments and techniques. However, it should be understood that many variations and modifications may be made while remaining within the spirit and scope of the invention.

What is claimed is:

1. A therapeutic method comprising preventing or treating a glutamate-related disorder in a mammal, by administering to said mammal an effective amount of a compound of the formula I:

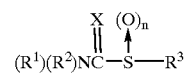

wherein a) $R^1$ and $R^2$ are individually $(C_1-C_8)$ alkyl, $(C_6-C_{12})$aryl, or heteroaryl; or $R^1$ and $R^2$ together with the nitrogen to which they are attached are a 4–8 membered ring optionally comprising 1, 2, or 3 additional heteroatoms selected from the group consisting of non-peroxide oxygen, sulfur, and $N(R_a)$, wherein each $R_a$ is absent or is hydrogen, $(C_1-C_8)$alkyl, $(C_1-C_8)$alkanoyl, phenyl, benzyl, or phenethyl; and $R^3$ is hydrogen, $(C_1-C_8)$ alkyl, $(C_6-C_{12})$aryl, heteroaryl, $SC(=S)N(R^1)(R^2)$, or a glutathione derivative; or b) $R^1$ and $R^3$ together are a divalent ethylene or propylene chain and $R^2$ is $(C_1-C_8)$ alkyl, $(C_6-C_{12})$aryl, or heteroaryl; or c) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene, ethylene, or a direct bond; and wherein the ring comprising $R_b$ and $R^3$ is a five- or six-membered ring;

wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;

X is O or S; and n is 0, 1, or 2;

or a pharmaceutically acceptable salt thereof.

2. The method of claim 1 wherein the glutamate-related disorder is a neurodegenerative disease.

3. The method of claim 2, wherein the neurodegenerative disease Huntington's disease, Alzheimer's disease, Parkinson's disease, aquired immunodeficiency syndrome, epilepsy, nicotine addiction, cerebral ischemia, or familial Amyotrophic Lateral Sclerosis.

4. The method of claim 2, wherein the neurodegenerative disease is Wernicke-Korsakoff syndrome, cerebral beriberi, Machado-Joseph disease, or Soshin disease.

5. The method of claim 1 wherein the glutamate-related disorder is anxiety, glutamate related convulsions, hepatic encephalopathy, neuropathic pain, domoic acid poisoning, hypoxia, anoxia, mechanical trauma to the nervous system, hypertension, alcohol withdrawal seizures, alcohol craving, cardiovascular ischemia, oxygen-induced seizures, or hypoglycemia.

6. The method of claim 1 wherein the glutamate-related disorder is anxiety, glutamate related convulsions, hepatic encephalopathy, domoic acid poisoning, hypoxia, anoxia, alcohol withdrawal seizures, alcohol craving, oxygen-induced seizures, or hypoglycemia.

7. The method of claim 1 wherein the glutamate-related disorder is anxiety.

8. The method of claim 1 wherein the glutamate-related disorder is glutamate related convulsions.

9. The method of claim 1 wherein the glutamate-related disorder is alcohol withdrawal seizures.

10. The method of claim 1 wherein the glutamate-related disorder is alcohol craving.

11. The method of claim 1 wherein the glutamate-related disorder is oxygen-induced seizures.

12. The method of claim 1 wherein the glutamate-related disorder is neuropathic pain.

13. The method of claim 1 wherein the glutamate-related disorder is Huntington's disease.

14. The method of claim 1 wherein the glutamate-related disorder is cerebral ischemia.

15. The method of claim 1 wherein the glutamate-related disorder is epilepsy.

16. The method of claim 1 wherein the compound is S-methyl-N,N-diethylthiolcarbamate sulfoxide.

17. The method of claim 1 wherein the compound is S-methyl-N,N-diethyldithiocarbamate sulfoxide.

18. The method of claim 1 wherein the compound is S-methyl-N,N-dimethylthiolcarbamate sulfoxide.

19. The method of claim 1 wherein the compound is S-methyl-N,N-dipropylthiolcarbamate sulfoxide.

20. The method of claim 1 wherein $R^1=R^2=$ethyl.

21. The method of claim 1 wherein X is O.

22. The method of claim 1 wherein X is S.

23. The method of claim 1 wherein $R^1$ and $R^2$ are individually $(C_1-C_8)$alkyl or $(C_6-C_{12})$aryl; $R^3$ is $(C_1-C_8)$ alkyl, H, SC(=S)N($R^1$)($R^2$) or a glutathione derivative; X is O or S; and n is 0 or 1, or a pharmaceutically acceptable salt thereof.

24. A method comprising inhibiting or preventing glutamate binding to mammalian neurotransmitter receptors, by contacting mammalian tissue comprising said receptors with an amount of a compound of formula (I):

(I)

wherein
a) $R^1$ and $R^2$ are individually $(C_1-C_8)$alkyl, $(C_6-C_{12})$aryl, or heteroaryl; or $R^1$ and $R^2$ together with the nitrogen to which they are attached are a 4–8 membered ring optionally comprising 1, 2, or 3 additional heteroatoms selected from the group consisting of non-peroxide oxygen, sulfur, and N($R_a$), wherein each $R_a$ is absent or is hydrogen, $(C_1-C_8)$alkyl, $(C_1-C_8)$alkanoyl, phenyl, benzyl, or phenethyl; and $R^3$ is hydrogen, $(C_1-C_8)$ alkyl, $(C_6-C_{12})$aryl, heteroaryl, SC(=S)N($R^1$)($R^2$), or a glutathione derivative; or
b) $R^1$ and $R^3$ together are a divalent ethylene or propylene chain and $R^2$ is $(C_1-C_8)$ alkyl, $(C_6-C_{12})$aryl, or heteroaryl; or
c) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene, ethylene, or a direct bond; and wherein the ring comprising $R_b$ and $R^3$ is a five- or a six-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;
X is O or S; and
n is 0, 1, or 2;
or a pharmaceutically acceptable salt thereof; wherein the amount is effective to block or reduce the binding of glutamate to said receptors.

25. A compound of formula I:

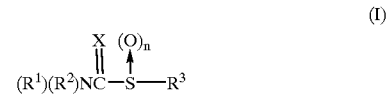

(I)

wherein
a) $R^1$ and $R^3$ together are a divalent ethylene or propylene chain and $R^2$ is $(C_1-C_8)$ alkyl, $(C_6-C_{12})$aryl, or heteroaryl; or
b) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene, ethylene, or a direct bond; and wherein the ring comprising $R_b$ and $R^3$ is a five- or a six-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;
X is O or S; and
n is 1;
or a pharmaceutically acceptable salt thereof.

26. A pharmaceutical composition comprising a compound of formula I:

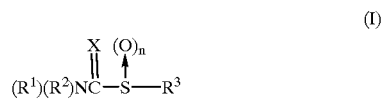

(I)

wherein
a) $R^1$ and $R^3$ together are a divalent ethylene or propylene chain and $R^2$ is $(C_1-C_8)$ alkyl, $(C_6-C_{12})$aryl, or heteroaryl; or
b) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene or a direct bond; and wherein the ring comprising $R_b$ and $R^3$ is a five- or a six-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;
X is O or S; and
n is 0, 1, or 2;
or a pharmaceutically acceptable salt thereof;
and a pharmaceutically acceptable carrier.

27. A compound of formula I:

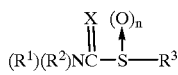

wherein
a) $R^1$ and $R^3$ together are a divalent ethylene or propylene chain and $R^2$ is $(C_1-C_8)$alkyl, $(C_6-C_{12})$aryl, or heteroaryl; or
b) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene, ethylene; or a direct bond; and wherein the ring comprising $R_b$ and $R^3$ is a five- or a six-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;
X is S; and
n is 2;
or a pharmaceutically acceptable salt thereof.

28. A compound of formula I:

wherein
$R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene, ethylene; or a direct bond; and wherein the ring comprising $R_b$ and $R^3$ is a five- or a six-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;
X is O or S; and
n is 2;
or a pharmaceutically acceptable salt thereof.

29. A compound of formula I:

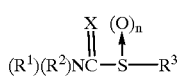

wherein
$R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene, ethylene; or a direct bond; and wherein the ring comprising $R_b$ and $R^3$ is a five- or a six-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;
X is O; and
n is 0, 1, or 2;
or a pharmaceutically acceptable salt thereof.

30. A pharmaceutical composition comprising a compound of formula I:

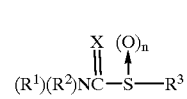

wherein
a) $R^1$ and $R^3$ together are a divalent ethylene or propylene chain and $R^2$ is $(C_1-C_8)$alkyl, $(C_6-C_{12})$aryl, or heteroaryl; or
b) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene, ethylene; or a direct bond; and wherein the ring comprising $R_b$ and $R^3$ is a five- or a six-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;
X is O; and
n is 0, 1, or 2;
or a pharmaceutically acceptable salt thereof; and a pharmaceutically acceptable carrier.

31. A pharmaceutical composition comprising a compound of formula I:

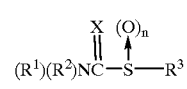

wherein
a) $R^1$ and $R^3$ together are a divalent ethylene or propylene chain and $R^2$ is $(C_1-C_8)$alkyl, $(C_6-C_{12})$aryl, or heteroaryl; or
b) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene, ethylene; or a direct bond; and wherein the ring comprising $R_b$ and $R^3$ is a five-membered ring;
wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;

X is O or S; and n is 0, 1, or 2;

or a pharmaceutically acceptable salt thereof.

32. A pharmaceutical composition comprising a compound of any one of claims 26, 27, 28, and 29; and a pharmaceutically acceptable carrier.

33. A compound of the formula I:

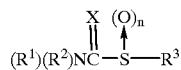
(I)

wherein

R$^1$ and R$^2$ are individually $(C_1-C_8)$alkyl, $(C_6-C_{12})$aryl, or heteroaryl; or R$^1$ and R$^2$ together with the nitrogen to which they are attached are a 4–8 membered ring optionally comprising 1, 2, or 3 additional heteroatoms selected from the group consisting of non-peroxide oxygen, sulfur, and N(R$_a$), wherein each R$_a$ is absent or is hydrogen, $(C_1-C_8)$alkyl, $(C_1-C_8)$alkanoyl, phenyl, benzyl, or phenethyl; wherein any aryl or heteroaryl in R$^1$ or R$^2$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;

R$^3$ is a glutathione derivative;

X is O or S; and n is 0, 1, or 2;

or a pharmaceutically acceptable salt thereof; provided the compound is not S-(N,N-diethylcarbamoyl)glutathione.

34. A pharmaceutical composition comprising a compound of the formula I:

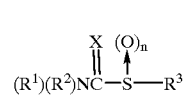
(I)

wherein

R$^1$ and R$^2$ are individually $(C_1-C_8)$alkyl, $(C_6-C_{12})$aryl, or heteroaryl; or R$^1$ and R$^2$ together with the nitrogen to which they are attached are a 4–8 membered ring optionally comprising 1, 2, or 3 additional heteroatoms selected from the group consisting of non-peroxide oxygen, sulfur, and N(R$_a$), wherein each R$_a$ is absent or is hydrogen, $(C_1-C_8)$alkyl, $(C_1-C_8)$alkanoyl, phenyl, benzyl, or phenethyl; wherein any aryl or heteroaryl in R$^1$ or R$^2$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;

R$^3$ is a glutathione derivative;

X is O or S; and n is 0, 1, or 2;

or a pharmaceutically acceptable salt thereof; and a pharmaceutically acceptable carrier.

35. The method of claim 1 wherein the compound is N,N-diethyl-S-carbamoyl-glutathione.

* * * * *

UNITED STATES PATENT AND TRADEMARK OFFICE
CERTIFICATE OF CORRECTION

PATENT NO. : 6,156,794
DATED : December 5, 2000
INVENTOR(S) : Faiman et al

It is certified that error appears in the above-identified patent and that said Letters Patent is hereby corrected as shown below:

In column 2, line 21, insert --)-- after "($C_1$-$C_8$".

In column 5, line 3, delete "requsite" and insert --requisite--, therefor.

In column 5, line 5, delete "requsite" and insert --requisite--, therefor.

In column 5, line 26, delete "requsite" and insert --requisite--, therefor.

In column 8, line 32, delete "$H_2O$." and insert --$H_2O$).--, therefor.

In column 13, line 33, delete "brining" and insert --bringing--, therefor.

In column 13, line 50, delete "form" and insert --from--, therefor.

UNITED STATES PATENT AND TRADEMARK OFFICE
CERTIFICATE OF CORRECTION

PATENT NO. : 6,156,794
DATED : December 5, 2000
INVENTOR(S) : Faiman et al

It is certified that error appears in the above-identified patent and that said Letters Patent is hereby corrected as shown below:

In column 16, line 35, delete "treatedanimals" and insert --treated animals--, therefor.

In column 16, line 41, insert --)-- after "animals".

In column 17, line 17, delete "experiments." and insert --experiments--, therefor.

In column 21, line 43, delete "ethylene;" and insert --ethylene,--, therefor.

In column 22, line 2, delete "ethylene;" and insert --ethylene,--, therefor.

In column 22, line 32, delete "ethylene;" and insert --ethylene,--, therefor.

In column 23, line 8, delete "26" and insert --25--, therefor.

Signed and Sealed this

Twenty-fourth Day of April, 2001

Attest:

NICHOLAS P. GODICI

*Attesting Officer*   *Acting Director of the United States Patent and Trademark Office*